(12) United States Patent
Trump

(10) Patent No.: US 9,429,460 B2
(45) Date of Patent: Aug. 30, 2016

(54) LIQUID LEVEL MONITORING

(71) Applicant: Martin Trump, Pforzheim (DE)

(72) Inventor: Martin Trump, Pforzheim (DE)

(73) Assignee: STRATEC Biomedical AG, Birkenfeld (DE)

( * ) Notice: Subject to any disclaimer, the term of this patent is extended or adjusted under 35 U.S.C. 154(b) by 497 days.

(21) Appl. No.: 13/758,305

(22) Filed: Feb. 4, 2013

(65) Prior Publication Data

US 2013/0319108 A1    Dec. 5, 2013

(30) Foreign Application Priority Data

Feb. 6, 2012    (GB) .................................. 1201983.2

(51) Int. Cl.

| G01F 23/26 | (2006.01) |
|---|---|
| G01F 11/00 | (2006.01) |
| G01F 23/00 | (2006.01) |
| G01F 11/26 | (2006.01) |
| G01N 35/10 | (2006.01) |

(52) U.S. Cl.
CPC ............ G01F 23/263 (2013.01); G01F 11/00 (2013.01); G01F 11/263 (2013.01); G01F 23/00 (2013.01); G01N 35/1011 (2013.01); G01N 2035/1025 (2013.01)

(58) Field of Classification Search
CPC .................................................. G01F 23/263
USPC ........................................... 73/304 C, 290 R
See application file for complete search history.

(56) References Cited

U.S. PATENT DOCUMENTS

| 4,326,851 | A | * | 4/1982 | Bello | .................... G01F 23/265 |
| | | | | | 141/198 |
| 4,736,638 | A | * | 4/1988 | Okawa | .................... G01F 23/24 |
| | | | | | 73/304 C |
| 5,639,426 | A | * | 6/1997 | Kerr | ....................... B01L 3/0275 |
| | | | | | 422/501 |
| 6,148,666 | A | | 11/2000 | Roesicke | |
| 7,976,794 | B2 | | 7/2011 | Trump | |
| 8,075,840 | B2 | * | 12/2011 | Shimane | ............... G01F 23/265 |
| | | | | | 422/500 |
| 8,096,177 | B2 | * | 1/2012 | Burris | ......................... 73/290 V |
| 8,689,625 | B2 | * | 4/2014 | Burkart et al. | ................. 73/295 |
| 2005/0178792 | A1 | * | 8/2005 | Knepler | ............... G01F 13/006 |
| | | | | | 222/1 |
| 2005/0279287 | A1 | * | 12/2005 | Kroeker | ................... A01K 7/00 |
| | | | | | 119/72 |
| 2007/0207259 | A1 | * | 9/2007 | Kulkarni | .................. G03F 7/16 |
| | | | | | 427/8 |

(Continued)

FOREIGN PATENT DOCUMENTS

| DE | 10 2006 034245 A1 | 1/2008 |
| DE | 10 2010 049 037 | 4/2012 |

(Continued)

*Primary Examiner* — Hezron E Williams
*Assistant Examiner* — Hoang Nguyen
(74) *Attorney, Agent, or Firm* — 24IP Law Group; Timothy R DeWitt

(57) ABSTRACT

A method and an apparatus for filling at least one liquid into at least one cavity. The method comprises filling a predetermined filling volume of the at least one liquid into the at least one cavity and determining if the liquid in the at least one cavity reaches a first liquid level in the at least one cavity. Filling the predetermined filling volume of the at least one liquid and the determining if the first level has not been reached, is repeated until enough volume of the at least one liquid has been added to the cavity or if the first level has been reached. The predetermined filling volume is equal to or smaller than a buffer volume above the first liquid level in the at least one cavity.

5 Claims, 3 Drawing Sheets

(56) References Cited

U.S. PATENT DOCUMENTS

| | | | |
|---|---|---|---|
| 2008/0168946 A1* | 7/2008 | Nam | C23C 16/52 118/726 |
| 2009/0165726 A1* | 7/2009 | Springer et al. | 119/14.02 |
| 2012/0024055 A1* | 2/2012 | Knight | G01F 23/263 73/304 C |
| 2012/0096940 A1 | 4/2012 | Burkart | |
| 2012/0228325 A1 | 9/2012 | Randall | |
| 2013/0065797 A1* | 3/2013 | Silbert | G01F 23/265 506/39 |
| 2014/0123774 A1* | 5/2014 | Tanoue | G01N 35/1009 73/863.01 |

FOREIGN PATENT DOCUMENTS

| | | |
|---|---|---|
| EP | 0 913 671 | 10/1998 |
| EP | 2 031 409 A2 | 3/2009 |
| EP | 2 031 499 | 3/2009 |
| GB | 2116530 * | 3/1982 |
| GB | 2116530 | 9/1983 |

* cited by examiner

LIQUID LEVEL MONITORING

CROSS-REFERENCE TO RELATED APPLICATIONS

This application claims benefit of and priority to UK Patent Application No. GB1201983.2 "Liquid Level Monitoring" filed on 6 Feb. 2012.

BACKGROUND OF THE INVENTION

1. Field of the Invention

The present disclosure relates to liquid handling and dispensing small amounts of liquids. The present disclosure relates to the field of diagnostics and a method, a system and an apparatus for filling a cavity with a liquid.

2. Introduction and Related Art

Handling of liquids in the microliter or milliliter range is important in many automated processes in biology, biochemistry, chemistry as well as in clinical or laboratory diagnostics and pharmaceutical research. Present liquid handling systems can handle a plurality of liquids in the same time and liquids are mixed, transferred and added in cavities or wells. Different types of cavities for liquid handling are known which can be used for handling single probes up to high throughput systems for handling large numbers of probes in parallel. For example, 96 well plates or well plates with other numbers of cavities are frequently used. Many liquid handling systems are highly automated and can handle a variety of liquids with high precision in short time intervals making these methods suitable for high throughput techniques.

Known systems have one or more pipettes or dispensing needles that allow the pipetting and dispensing of liquids in different cavities in series and/or in parallel.

In case several liquids are mixed in a cavity or several liquids have to be added to a single cavity, there is a risk that the cavities are overloaded and the liquid is spilled which may lead to contamination of neighbouring cavities and of the apparatus. Such contamination often requires expensive and extensive cleaning of the apparatus and can destroy valuable samples. Overfilling and subsequent contamination should be avoided. In many cases, however, a cavity is already filled with an unknown residual volume of liquid at the start of a liquid handling process. In this case, the residual volume has to be determined in order to avoid overfilling and spilling of the cavity.

Liquid level detectors are used in order to control the filling of cavities and to avoid overflow contamination and spilling of the liquids.

EP 0 913 671 (also published as U.S. Pat. No. 6,148,666) discloses a capacitive liquid level detector attached to a filling needle for determining if the filling needle is in contact with a liquid in the cavity.

DE 10 20060034245-A also describes a dispensing needle that may be equipped with a barometric or capacitive liquid level detection in order to detect the presence of a liquid in a cavity.

EP 2 031 499 discloses an apparatus and a method for detecting the level of liquid in a cavity to determine the amount of liquid present in the cavity. This method requiring the liquid level detector into the cavity until the detector comes into contact with the liquid surface.

SUMMARY OF THE INVENTION

The present disclosure proposes a method and an apparatus for filling at least one liquid into at least one cavity. The method comprises filling a predetermined filling volume of the at least one liquid into the at least one cavity and determining if the liquid in the at least one cavity reaches a first liquid level in the at least one cavity. Filling the predetermined filling volume of the at least one liquid and the determining if the first level has not been reached, is repeated until enough volume of the at least one liquid has been added to the cavity or if the first level has been reached. The predetermined filling volume is equal to or smaller than a buffer volume above the first liquid level in the at least one cavity. No liquid can be spilled and an overflow of liquid is reliably avoided. The buffer volume is equal to or larger than the filling volume and liquid can be added until the liquid is determined at the first level. The process will be stopped and no additional predetermined filling volume will be added to the cavity as soon as a positive signal at the first liquid level has been determined.

The determining can be performed directly during filling or the determining and the filling can be performed alternating in sequence i.e. first filling a first predetermined filling volume, then determining if the liquid level in the at least one cavity has reached the first liquid level. If the first liquid level has not been reached, a second predetermined filling volume that is identical to the first predetermined filling volume is added. Then again, it is determined whether the liquid level has reached the first liquid level. These first steps are repeated until enough liquid has been added or until the first liquid level is reached.

The liquid level detection may be performed using a capacitive liquid level detection.

The liquid level detection may be performed at the opening of a dispensing device that is moved into the at least one cavity. However, it is also possible to use a separate detector that can be moved and placed in the cavity independently from the dispensing device.

The buffer volume may be the volume in the top part of the cavity and may be determined such that a predetermined filling volume can be added above the first liquid level without overflow or spilling of the at least one liquid.

The buffer volume can be determined by a fixed value or can be modified in dependence of the predetermined filling volume. For example, a first liquid may be added with a first predetermined filling volume and a second volume may be added later to the same cavity with a second predetermined filing volume. A second buffer volume may be determined if the second predetermined filling volume is different from the first predetermined filling volume.

The present disclosure also relates to an apparatus for filling the at least one liquid into at least one cavity.

BRIEF DESCRIPTION OF THE DRAWINGS

The invention will now be described with respect to the accompanying drawings that are given as pure illustrative examples only and in which.

DETAILED DESCRIPTION

The present disclosure will now be described in more detail with respect to detailed examples that implement different aspects of the present disclosure. It is to be understood that not all features of the present examples need to be implemented in order to carry out the invention and a person skilled in the art will select and modify those features that he considers appropriate for a specific application. It will be understood that features of one aspect or embodiment of the invention can be combined with a feature of a different aspect or aspects and/or embodiments of the invention.

Figure 1A:
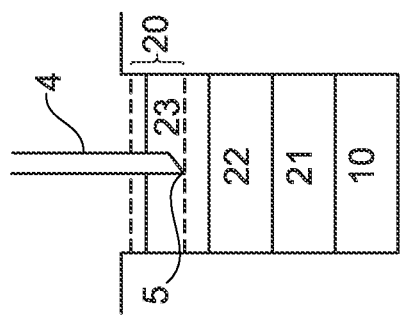
FIGS. 1A-1D and 2A-2B show examples of how a liquid is filled into a cavity according to the present invention.

FIG. 1A shows a cavity 2 with a dispensing device such as, but not limited to, a dispensing needle 4, which can be inserted into the cavity 2. In the starting position shown in FIG. 1A the dispensing needle 4 is removed from the cavity 2. The dispensing needle 4 has a capacitive liquid level detector 5 at its tip. While the capacitive liquid level detector 5 is show integrated into the dispensing needle 4, the capacitive liquid level detector 5 can also be provided separately. The cavity 2 may be a reaction cavity and can be any cavity useful in chemical, biochemical or biological or pharmaceutical of diagnostic processes. The cavity may be a tube, a cuvette, a flask, a glass tube, a well such as a micro titre plate or other types of well plates (for example 96 or 384 well plates) or their like. The teachings of the disclosure can be applied to any reaction cavity and any cavity may be used.

The dispenser needle 4 may be any dispenser needle or dispensing system typically used in state of the art dispensing systems and a known dispensing system may be adapted to the present disclosure. A dispensing tip or dispensing needle 4 may be used for suction and dispensing of liquids or a liquid may be pumped through the dispensing system. The dispensing device 4 can be a metal needle or can be a disposal system that is be replaced after use.

The present description is given with respect to a single cavity and a single dispensing needle. It is obvious to a person skilled in the art that a plurality of cavities can be used that are arranged in parallel and/or in series. The same needle can be used for several cavities or a plurality of dispensing needles 4 can be used in parallel or in series.

The cavity 2 may contain an unknown residual volume 10. It is in many cases not possible to exactly know or determine the residual volume 10 or determination would require specific sensors. The residual or starting volume 10 is not known and it is therefore not unknown how much liquid can be added before the cavity 2 is filled or overfilled.

A buffer volume 20 is defined corresponding to a filling volume of liquid that shall be added to the cavity in one filling step. The buffer volume 20 is equal or larger than the filling volume of the subsequent filling step. A lower level 20a of the buffer volume 20 is determined corresponding to the level, at which the buffer volume 20 can be additionally added to the cavity without overflow or spilling of the liquid.

Figure 1B:
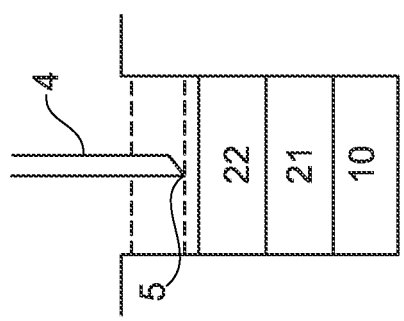
Figure 1C:
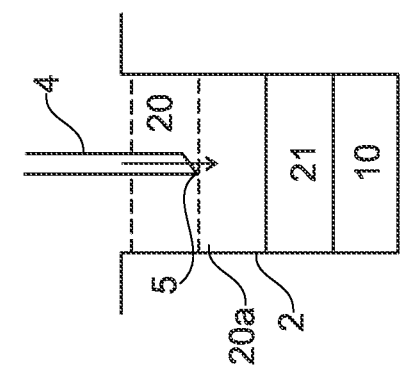

The dispensing needle 4 is inserted into the cavity to a position at which the liquid level detector 5 is at the lower level 20a of the buffer volume 20 as indicated in FIG. 1B. After the dispensing needle 4 is inserted into the cavity 2, a first one 21 of the filling volume of a first liquid is added into the cavity 2. In the case shown in FIG. 1B the liquid level in the cavity is now on top of the first one 21 of the filling volume and is still below the lower limit of the buffer volume 20. The liquid level detector 5 does not detect any liquid at this stage. A second one 22 of the filling volume is added to the cavity as shown in FIG. 1C. In the case shown the first on 21 and the second on 22 of the filling volume have exactly the same volume. The liquid can be the same or can be different liquid in both steps.

As shown in FIG. 1C, the top level of the second one of the filling volume 22 is still lower than the liquid level detector 5 and no liquid is detected at the liquid level detector 5. If enough liquid has been added to the cavity 2, the filling process can be terminated, the dispensing needle 4 is removed and the filling process can be continued otherwise or stopped. No cleaning of the dispensing needle is required and the needle may be directly used in another cavity.

Figure 1D:
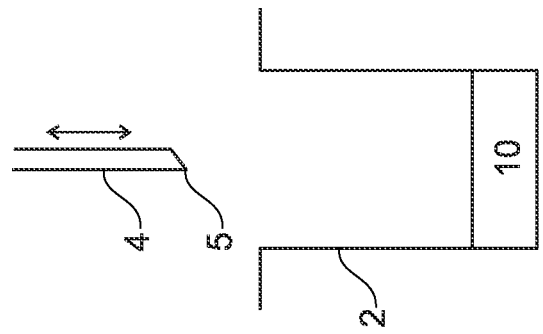

If more liquid should be added, a third one 23 of the filling volume may be added as shown in FIG. 1D. Now the liquid level has reached the liquid level detector 5 and the presence of liquid is detected. Therefore, the filling process is stopped and the dispensing needle 4 is removed from the cavity. The dispensing needle 4 may be cleaned or replaced if needed. An error signal may be issued.

The buffer volume 20 is equal to or larger to the first one 21, the second one 22, and the third one 23 of the filling volume. Therefore overflow and spilling of the liquid is avoided and the process is stopped before overfilling occurs independently of the starting volume 10.

The buffer volume 20 and the first one 21, the second one 22, and the third one 23 of the filling volume can be selected depending on each other as long as it is ensured that the buffer volume 20 is equal to or larger than the volume filled into the cavity. The first one 21, the second one 22, and the third one 23 of the filling volume may have the identical volume (as indicated in FIGS. 1A-D and 2A-B) or may have different volumes. In case of different volumes, the buffer volume 20 may correspond to the largest one of the first one 21, the second one 22, and the third one 23 of the filling volume or the buffer volume 20, and consequently the position of the needle 4 with the sensor 5 may be adjusted for each filling step.

While the present disclosure refers to the first one 21, the second one 22, and the third one 23 of the filling volume, it is obvious that the disclosure is not limited to this number and a greater or fewer number of filling volumes can be used.

Figure 2B:
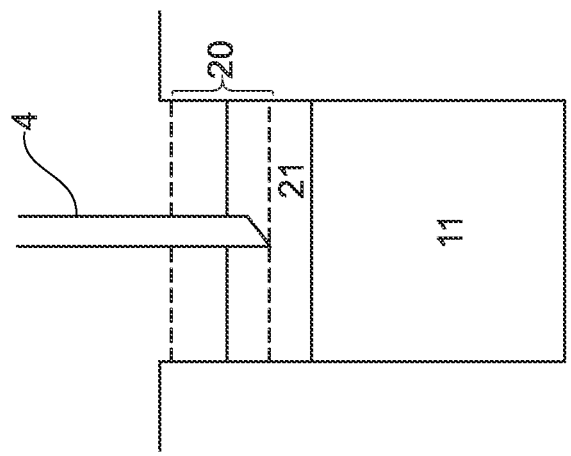
Figure 2A:
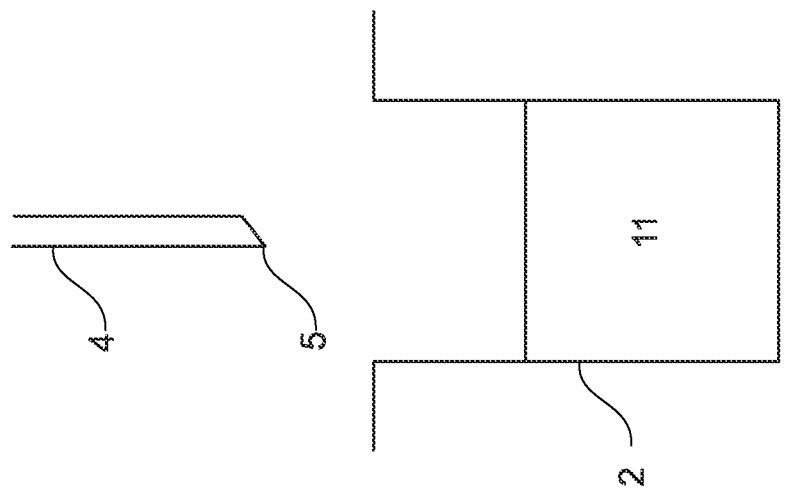

FIGS. 2A-2B show the example of FIGS. 1A-1D with a larger amount of residual or starting liquid 11. The cavity 2 is pre-filled with a larger amount of liquid 11. If now a first one of the filling volume 21 is added to the cavity, the liquid level detection detects the liquid at the first level 20a and a positive signal is issued showing that the cavity 2 is already filled and no further filling is possible. In this case, the dispensing needle 4 is removed and error signal may be issued indicating that the cavity 2 was not filled correctly and should not be removed from consideration of further processing.

It may also be determined if the diagnostic method is interrupted or if sufficient liquid has been added to continue the diagnostics process.

Spilling or overflow of liquid and contamination of the apparatus as wells as of neighbouring cavities is reliably avoided.

The several processing steps have been described as a sequence of processing steps but it is possible to carry out these steps in parallel or at least partially in parallel. For example, the filling of the cavity 2 with one of the filling volumes can be done while the detecting the liquid level at the liquid level detector 5. This allows accelerating the filling process. It is furthermore not necessary to determine the residual volume 10 or 11 prior to starting the filling steps.

Figure 3:
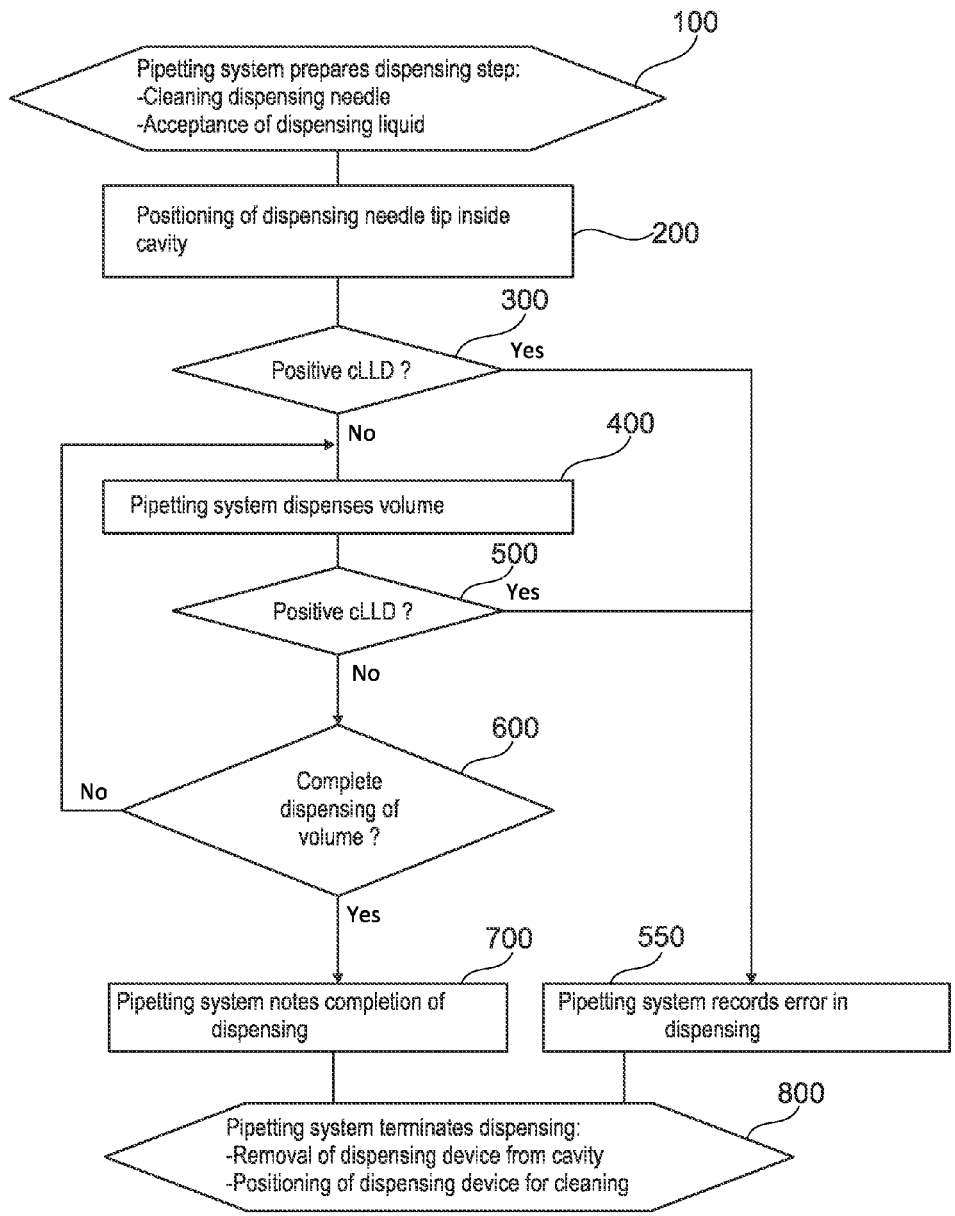
FIG. 3 shows a flow diagram of a method of the present disclosure.

FIG. 3 shows a flow diagram showing the steps of the present disclosure. The method starts with a preparation step 100 by preparing the pipetting system prior to dispensing. The preparation step 100 comprises a cleaning of the dispensing needle 4 and the acceptation of a dispensing liquid.

The pipetting system with the dispensing needle 4 and the liquid level detector 5 are positioned with the tip of the dispensing needle 4 inside the cavity 2 (step 200) such that the liquid level detector 5 is at the lower level 20a of the buffer volume 20.

The liquid level detector 5 determines in step 300 whether a liquid is detected at the first level 20a. In a case a liquid is detected, an error message 550 may be issued and the dispensing maybe interrupted in step 800. In case no liquid is detected in step 300 a first one 21 of the filling volume is added to the cavity 2 by the dispensing device 4. Subsequently the liquid level may be determined with liquid level detector 5 again (step 500). A message is displayed 300 and the dispensing is interrupted 800 if liquid level detector 5 has detected liquid. In case no liquid level is detected, it will be determined whether the complete volume has been dispensed (step 600). The system returns to step 400 in case the complete volume has not yet been dispensed and a further filling volume 22 or 23 will be added to cavity 2. If the complete liquid has been added, a signal may be output indicating that dispensing was successful (step 700) and the pipetting system may terminate the dispensing (step 800) for example by removing the dispensing device 4 from the cavity 2 and optionally by cleaning the dispensing device 4 and/or the liquid level detector 5.

A person skilled in the art will understand that the present disclosure can be used in different ways. The predetermined volume of the liquid may be added until the liquid level detector 5 detects the presence of the liquid at the lower lever 20a of the buffer volume 20. It is also possible to stop the filling process after predetermined number of filling steps or filling volumes 21, 22, 23 if the required amount of liquid has been added. In this case the liquid level detector 5 and the dispensing device 4 do not come into liquid contact with the liquid inside the cavity 2 thy can be reused as long as no liquid has reached the liquid level detector 5. This allows filling of multiple cavities without time consuming and extensive cleaning steps.

A person skilled in the art will also understand that the predetermined filling volumes can be varied to a filling and can be adapted according to the specific needs. Changing or adapting the predetermined filling volumes requires a modification of the buffer volume 20. It has to be ensured that the buffer volume 20 is equal to or larger than the actual filling volume. For example, it may be possible to add first one 21 of the filling volume liquid with a large volume. In this case the buffer volume will be larger and the liquid level detector 5 has to be at a lower position in the cavity 2. Then a second filing volume different from the first filling volume may be added providing a smaller amount of liquid than the first filling volume. In this case, the liquid level detector can remain at the same place but can also be placed at a higher position such that a smaller buffer volume is used and more liquid can be added to the cavity 2. The filling volume can be free selected as long as it is smaller than the volume of the cavity 2 and the buffer volume 20.

The invention claimed is:

1. A method for filling at least one liquid into at least one cavity, the method comprising:
   inserting a dispensing needle into the at least one cavity to a position at which a liquid level detector is at a lower level of a buffer volume;
   detecting with the liquid level detector whether a first liquid level in the at least one cavity is reached;
   filling a pre-determined filling volume of the at least one liquid into the at least one cavity if the first liquid level is not reached;
   determining if the at least one liquid in the at least one cavity reaches the first liquid level in the at least one cavity; and
   repeating the steps of filling the pre-determined filling volume of the at least one liquid and the determining, if the first liquid level has not been reached;
   wherein the pre-determined filling volume is equal to or smaller than the buffer volume at whose lower level the liquid level detector is positioned above the first liquid level in the at least one cavity.

2. The method of claim 1, wherein the determining if the first liquid level is reached comprises using a capacitive liquid level detection.

3. The method of claim 1, further comprising placing an opening of a dispensing device in the at least one cavity.

4. The method of claim 3, wherein the determining if the first liquid level is reached comprises detecting a contact of the liquid at the first liquid level with the dispensing device.

5. The method of claim 1, wherein the buffer volume is equal or smaller than a volume defined between the first liquid level and a level in the at least one cavity, where the liquid spills out of the at least one cavity.

* * * * *